United States Patent [19]

Gutowski

[11] 3,960,836

[45] June 1, 1976

[54] ACYLATED DERIVATIVES OF PYRAZOFURIN AND PROCESS FOR THEIR PREPARATION

[75] Inventor: Gerald E. Gutowski, Indianapolis, Ind.

[73] Assignee: Eli Lilly and Company, Indianapolis, Ind.

[22] Filed: July 22, 1974

[21] Appl. No.: 490,627

[52] U.S. Cl.................. 260/210 AB; 260/209 R; 260/310 R; 424/180
[51] Int. Cl.² ........................................ C07H 7/06
[58] Field of Search .......... 260/210 R, 210 AB, 209

[56] References Cited
UNITED STATES PATENTS

| | | | |
|---|---|---|---|
| 3,674,774 | 7/1972 | Williams et al............... | 260/210 AB |
| 3,798,209 | 3/1974 | Witkowski et al. .......... | 260/211.5 R |

OTHER PUBLICATIONS

Henion et al., Biochimica Et Biophysica Acta, vol. 148 (1967) pp. 106–113.

*Primary Examiner*—Donald B. Moyer
*Attorney, Agent, or Firm*—Charles W. Ashbrook; Walter E. Buting; Everet F. Smith

[57] ABSTRACT

A process for preparing new compounds which are N- and O-acylates of pyrazofurin comprises first selective mono-N-acylation under non-basic conditions in an organic solvent. The mono-N-acylate so formed is further acylated under mild basic conditions to provide a tetra-acylated or penta-acylated pyrazofurin derivative, depending upon the duration of reaction. Mild solvolysis of either a tetra-acylate or a penta-acylate provides a tri-acylated pyrazofurin derivative. In the presence of a strong base, the mono-N-acylate is further acylated to provide different tetra-acylates or penta-acylates of pyrazofurin, again depending upon the duration of reaction. Pyrazofurin acylates are useful as antiviral, antipsoriatic, and antifungal agents, as well as intermediates for new C-nucleosides.

21 Claims, No Drawings

ACYLATED DERIVATIVES OF PYRAZOFURIN AND PROCESS FOR THEIR PREPARATION

BACKGROUND OF THE INVENTION

Pyrazofurin is a C-nucleoside antibiotic, 4-hydroxy-3-$\beta$-D-ribofuranoxylpyrazole-5-carboxamide, obtained initially by fermentation of a strain of *Streptomyces candidus*. In accordance with the nomenclature of the United States Adopted Names Council, pyrazofurin is the generic name which replaces the former generic name pyrazomycin. Methods for the production, recovery, purification, and characterization of pyrazofurin are described in detail in U.S. Pat. Nos. 3,674,774 and 3,802,999. Pyrazofurin has been shown to possess antiviral activity, for example against rhinovirus, measles, herpes simplex, and vaccinia viruses. In addition, pyrazofurin has exhibited antitumor activity against several carcinomas, as demostrated by Sweeney, et al., *Cancer Research*, 33, 2619-2623 (1973).

Extensive research has been directed to the study of antiviral agents and to potential antitumor agents in general. Difficulty has generally been encountered in the development of antiviral agents because viruses are intracellular parasites which rely on the metabolic processes of the invaded cell for their own existence. Consequently, agents which inhibit or kill the viruses may in addition injure the host cells that harbor them. Similarly, the severe systemic toxicity of many potentially useful antitumor agents generally limits their use.

Azauridine is one such antitumor agent which has been used successfully to produce partial remissions of acute leukemias in adults; however, the results obtained are generally only temporary. Large intravenous doses are required because of its poor absorption from the intestine, and sustained blood levels are difficult to maintain due to its rapid excretion. An orally effective triacetyl derivative of azauridine, Azaribine, has been prepared in an effort to increase effective blood levels of free azauridine. However, moderate anemia and neurological disturbances are common side effects accompanying triacetylazauridine usage.

Considerable interest has recently been directed to pyrazofurin, not only because of its antiviral and antitumor activities, but also because it is one of very few C-nucleosides showing antitumor activity. The complete chemical synthesis of pyrazofurin has recently been reported by Farkas, Flegelová, and Šorm, *Tetrahedron Letters*, 2279-2280 (1972). Panzica and Townsend have prepared several nucleosides which are structurally similar to pyrazofurin and which also display antitumor activity, *Journal of Organic Chemistry*, 36, 1594-1596 (1971).

It is an object of the present invention to provide novel C-nucleosides which are useful pharmacological agents. In particular, it is an object of this invention to provide certain acylated derivatives of pyrazofurin. Additionally, because normal acylation conditions when applied to pyrazofurin lead to very complex mixtures of partial and total acylates, it is a further object of this invention to provide processes whereby various partial acylates of pyrazofurin are cleanly prepared. A still further object of this invention is to provide new compounds which display antiviral, antifungal and are additionally useful as antipsoriatic agents.

SUMMARY OF THE INVENTION

This invention relates to certain acylated derivatives of pyrazofurin and to processes for their preparation. The invention is particularly directed to the preparation of certain O- and N-acylated pyrazofurin derivatives. More particularly, the invention is directed to certain mono-, di-, tri-, tetra-, and penta-acylates of pyrazofurin. The compounds provided by this invention have the formula

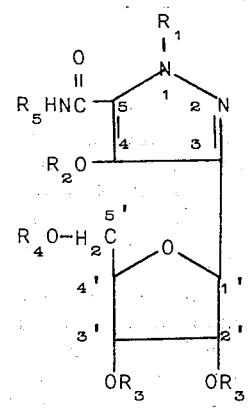

in which $R_1$, $R_2$, $R_3$, and $R_5$ independently are hydrogen or $C_1$—$C_6$ alkanoyl and $R_4$ is hydrogen, $C_1$—$C_6$ alkanoyl, palmitoyl, benzoyl, or adamantoyl, with the limitations that at least one of $R_1$, $R_2$, $R_3$, $R_4$, or $R_5$ is a group other than hydrogen, that $R_2$ is alkanoyl only when $R_1$ is alkanoyl, that $R_3$ is alkanoyl only when $R_4$ is alkanoyl; and that $R_5$ is alkanoyl only when $R_3$ and $R_4$ are both alkanoyl.

The compounds of this invention are prepared by the novel process which comprises as a first step the selective monoacylation of pyrazofurin with an acylating agent under non-basic conditions in an organic solvent to provide the mono-$N_1$-acylate. Further acylation of the mono-$N_1$-acylate under mild basic conditions for moderate periods of time provides a tetra-acylate, specifically a 2',3',5'-tri-O-acylate-$N_1$-acylate. When the mono-$N_1$-acylate is acylated under mild basic conditions for prolonged periods of time, a penta-acylate is recovered, namely a 4,2',3',5'-tetra-O-acylate-$N_1$-acylate. Solvolysis of either the tetra-acylate or the penta-acylate affords a 2',3',5'-tri-O-acylate. Acylation of the mono-$N_1$-acylate under more vigorous acylation conditions in the presence of a stronger base provides a different tetra-acylate, specifically one wherein the 5-carboxamide group is acylated along with the three hydroxyl groups of the ribofuranosyl moiety. By extending the length of reaction under the more basic acylation conditions, a different penta-acylated pyrazofurin derivative is formed, namely a 2',3',5'-tri-O-acylate-$N_1$-acylate wherein the 5-carboxamide group is also acylated.

DETAILED DESCRIPTION OF THE INVENTION

As hereinbefore indicated, the compounds of this invention have the formula

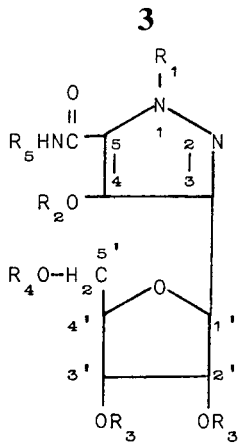

I $R_1$ in the above formula is hydrogen or $C_1$–$C_6$ alkanoyl. Examples of $C_1$–$C_6$ alkanoyl groups include both straight and branched chain carboxylic acid residues having no more than six carbons, such as formyl, acetyl, propionyl, n-butyryl, isobutyryl, n-pentanoyl, 2-methylbutyryl, pivaloyl, n-hexanoyl, 3-methyl-pentanoyl, 2,3-dimethylbutyryl, and the like. The most preferred alkanoyl groups are the straight chain alkanoyl groups such as acetyl or butyryl, for example.

$R_2$ in the above formula is hydrogen or $C_1$–$C_6$ alkanoyl, but is alkanoyl only when $R_1$ is alkanoyl. When $R_2$ is alkanoyl, it is preferably the same as $R_1$.

$R_3$ in the above formula is hydrogen or $C_1$–$C_6$ alkanoyl, but is alkanoyl only when $R_4$ is alkanoyl. Both $R_3$'s together can be a protecting group for the 2' and 3' hydroxyl groups of the ribofuranosyl ring system. "Protecting group" as used herein refers to common glycol protecting groups such as cyclic acetals and ketals, cyclic esters and orthoesters. Examples of typical protecting groups commonly used include isopropylidene ketal, benzylidene acetals, cyclohexylidene ketal, cyclic carbonates, thiocarbonates, and the like.

$R_4$ in the above formula is hydrogen, $C_1$–$C_6$ alkanoyl, palmitoyl, benzoyl, or adamantoyl.

$R_5$ in the above formula is hydrogen, or when $R_3$ and $R_4$ are alkanoyl, $R_5$ can be $C_1$–$C_6$ alkanoyl.

At least one of $R_1$, $R_2$, $R_3$, $R_4$, or $R_5$ of the above formula is other than hydrogen.

The compounds of the present invention are named according to standard naming systems by following the numbering system shown in the above formula. Pyrazofurin is described by the above formula when $R_1$, $R_2$, $R_3$, $R_4$, and $R_5$ are all hydrogen, and is systematically named 4-hydroxy-3-β-D-ribofuranosylpyrazole-5-carboxamide. As can be seen from the above formula, pyrazofurin is a C-nucleoside which contains six centers which are capable of reacting with acylating agents. In particular, the pyrazole ring portion of of pyrazofurin contains a nitrogen atom which can be acylated. Additionally, the pyrazole ring bears a 4-hydroxyl substituent and a 5-carboxamide substituent, both of which can be acylated. The ribofuranosyl portion of pyrazofurin can form ayclates at each of its three hydroxyl groups. It should be recognized that any reactive nitrogen or hydroxyl group of pyrazofurin can be acylated with essentially any acylating agent under appropriate conditions. For example, any acyl group can be attached at the pyrazole-$N_1$-position if desired.

The compounds of the present invention are prepared by selective acylation of pyrazofurin under controlled conditions of basicity, reaction temperataure, and duration of reaction. Depending upon the conditions of acylation, certain pyrazofurin mono-acylates, di-acylates, tri-acylates, tetra-acylates, and penta-acylates are prepared and isolated in good yield.

The normal procedure for preparing acylated derivatives of polyfunctional compounds such as pyrazofurin generally comprises exhaustive acylation in the presence of an acid binding agent. For example, lincomycin is fully acylated in the presence of an acylating agent and a base, as described in U.S. Pat. No. 3,318,866. When this general procedure is applied to pyrazofurin, a complex mixture of acylates comprising the mono-, di-, tri-, tetra-, penta-, and hexa-acylates are obtained in admixture with each other. Separation and purification of the individual partial acylates is extremely difficult and inefficient. Moreover, the yields of any particular partial acylate are quite low due to the concomitant production of other partial acylates as well as completely acylated products. Additionally, basic solution of pyrazofurin are known to equilibrate between different tautomeric forms of pyrazofurin, thus further complicating normal acylation.

In accordance with the invention, pyrazofurin is selectively mono-acylated at the pyrazole-$N_1$-position, thereby freezing the structure into one tautomeric form. Once the mono-$N_1$-acylate has been formed in accordance with the present invention, subsequent specific acylations are greatly simplified. In particular, certain di-, tri-, tetra-, and penta-acylates are conveniently prepared from the mono-$N_1$-acylate.

In one aspect of the present invention, pyrazofurin is first treated with an acylating agent in an organic solvent, in the absence of a base, to provide the corresponding mono-$N_1$-acylate. Any of a number of acylating agents can be used in the present process, the nature of the particular agent selected not being critical to the process. Typical acylating agents commonly used include acid halides, especially acid chlorides and acid bromides and most especially acid chlorides; acid anhydrides, including mixed acid anhydrides; ketenes, and the like. Generally, the acid anhydrides are the preferred acylating agents when the lower alkanoyl groups, such as acetyl, propionyl, and butyryl for example, are desired. When larger acyl groups such as benzoyl, palmitoyl, or adamantoyl for example, are desired, the corresponding acid halide is generally preferred. Examples of acid anhydrides routinely used include acetic anhydride, formic acetic anhydride, propionic anhydride, butyric anhydride, hexanoic anhydride, and the like. Typical acid halides which can be used include acetyl chloride, butyryl bromide, 3-methylpentanoyl chloride, benzoyl chloride, adamantoyl chloride, palmitoyl chloride, and the like. Examples of useful ketenes include ketene, ethylketene, propylketene, butylketene, isopropylketene, isobutylketene, and the like.

The mono-$N_1$-acylation reaction is carried out in an organic solvent such as an alcohol, for example, An alcohol such as methanol or ethanol is especially preferred when acylation of the hydroxyl groups of the ribofuranosyl portion of purazofurin is to be avoided, as in the case of mono-$N_1$-acylation for example. The alcoholic solvents are generally more reactive toward acylation than are the ribofuranosyl hydroxyl groups, and consequently will react with any excess acylating agent in the reaction mixture more rapidly than will the ribofuranosyl hydroxyl groups. Other solvents that can be used, for example as co-solvents if desired, include ketones such as acetone or methyl ethyl ketone; ethers such as diethyl ether or tetrahydrofuran, and the like.

The temperature of the mono-$N_1$-acylation reaction is generally maintained below about 40°C. The temperature is most conveniently maintained between about 0° to about 30°C., and in practice, the temperature is preferably maintained at about 02 to 25°C. The reactants, that is pyrazofurin and the desired acylating agent, can be commingled in about equimolar amounts; however, excess acylating agent is generally preferred. The acylating agent, preferably an acid anhydride or a ketene, is generally employed in about a 2 to 20 molar excess; however, more can be used if desired. Alternatively, when an acid halide is selected as the acylating agent, an approximately equimolar amount is preferably used. The mono-$N_1$-acylation reaction is substantially complete after about 30 to 90 minutes, especially when carried out at the preferred temperature of about 0° to 25°C. The pyrazofurin mono-$N_1$-acylate is conveniently isolated by removal of any solvent and excess acylating agent present in the reaction mixture, generally by evaporation. The product can be further purified, if desired, by standard procedures such as chromatography, crystallization, distillation, or the like. It should be noted, however, that the mono-$N_1$-acyl group is in general easily solvolyzed with protic solvents, especially water, and should therefore not be exposed to such conditions.

Illustrative examples of mono-$N_1$-acylates of pyrazofurin provided by the present invention include:

4-Hydroxy-3-$\beta$-D-ribofuranosyl-$N_1$-acetylpyrazole-5-carboxamide;

4-Hydroxy-3-$\beta$-D-ribofuranosyl-$N_1$-n-butyryl-pyrazole-5-carboxamide;

4-Hydroxy-3-$\beta$-D-ribofuranosyl-$N_1$-n-hexanoyl-pyrazole-5-carboxamide;

4-Hydroxy-3-$\beta$-D-ribofuranosyl-$N_1$-(2-methylbutyryl) pyrazole-5-carboxamide; and the like.

The mono-$N_1$-acylates of pyrazofurin are useful as antiviral agents and antipsoriatic agents. Additionally, the mono-$N_1$-acylates are useful as intermediates for the preparation of other acylated pyrazofurin derivatives, as described hereinbelow.

In another aspect of this invention, a pyrazofurin mono-$N_1$-acylate is further acylated in the presence of a week base, thereby providing either a tetra-acylate or a penta-acylate, depending upon the duration of the reaction. It should be understood that when more than one acyl group is present in a pyrazofurin derivative, it is possible to form mixed acylates, that is to say, acylates wherein not all of the acyl groups are the same.

The pyrazofurin mono-$N_1$-acylate is further acylated in the presence of a weak base. The term "weak base" refers to a base having $pK'_b$ in the range of about 7 to about 10. Typical weak bases commonly used include amines, especially arylamines and cyclic amines such as pyridine, dimethylaniline, piperazine, p-toluidine, and the like. Pyridine is an especially preferred weak base in the present process. The amount of base used is not critical, however, an excess of base is generally used. The amount of base generally is sufficient to serve as solvent or co-solvent. Alternatively, the acylation can be carried out in any of a number of organic solvents, if desired. If a solvent is desired, one can be selected from among the aromatics, such as benzene or toluene for example; or the halogenated hydrocarbons such as methylene chloride or chloroform; or the ethers, such as diethyl ether, tetrahydrofuran, or the like. These solvents can serve as co-solvents if desired, for example in conjunction with the acylating agent and the base.

The acylation is most conveniently carried out by using simply the weak base and the acylating agent as the reaction medium. More specifically, the acylation can best be carried out by commingling the acylating agent and the mono-$N_1$-acylate in an excess of a weak base, preferably pyridine, and stirring the reaction mixture for a time sufficient to effect either tetra-acylation or penta-acylation. The acylating agent, preferably an acid anhydride as described hereinabove, is used in excess of the mono-$N_1$-acylate. The excess normally amounts to about 10 to 20 molar excess; however, more can be used if desired. The preparation of the pyrazofurin tetra-acylated derivative is substantially complete after about 1 to about 3 hours when the reaction is carried out at a temperature of about −10° to about 15°C. The temperature can be increased if desired, for example, to about 25°C.; however, the reaction can best be controlled if the temperature is kept below about 15°C., preferably at about 2°C. The tetra-acylate that is formed is a pyrazofurin 2′, 3′, 5′-tri-O-acylate-$N_1$-acylate.

The preferred tetra-acylates are those wherein all four acyl groups are all the same alkanoyl group. The tetra-acylate is generally isolated by complete removal of any excess base, excess acylating agent, or any solvents present in the reaction mixture. Complete removal of any excess base or excess acylating agent can best be accomplished by repeatedly dissolving the product mixture in a suitable organic solvent or solvent mixture and subsequently distilling the solvent, thereby effectively removing any excess base or acylating agent. Solvents generally used for this purpose are aromatic solvents, such as benzene, toluene, or xylene, or alcohols such as methanol or ethanol. Mixtures of solvents can be used if desired; for example, a mixture of methanol and benzene or benzene and toluene is desirable. Once all of the excess acylating agent and excess base and any other solvent has been completely removed from the tetra-acylate, further purification of the product is generally not needed. Further purification can be accomplished if desired, however, by standard methods such as gas chromatography, column chromatography, and the like.

Typical examples of pyrazofurin 2′, 3′, 5′-tri-O-acylate-$N_1$-acylates prepared by the above-described process include, among others:

4-Hydroxy-3-$\beta$-D-(2′,3′,5′-tri-O-acetyl-ribofuranosyl)-$N_1$-acetylpyrazole-5-carboxamide;

4-Hydroxy-3-$\beta$-D-(2′,3′,5′-tri-O-n-butyryl-ribofuranosyl)-$N_1$-n-butyrylpyrazole-5-carboxamide;

4-Hydroxy-3-$\beta$-D-(2′,3′,5′-tri-O-n-hexanoyl-ribofuranosyl)-$N_1$-n-hexanoylpyrazole-5-carboxamide;

4-Hydroxy-3-$\beta$-D-(2′,3′,5′-tri-O-isobutyryl-ribofuranosyl)-$N_1$-acetylpyrazole-5-carboxamide;

4-Hydroxy-3-$\beta$-D-(2′,3′,5′-tri-O-n-butyryl-ribofuranosyl)-$N_1$-acetylpyrazole-5-carboxamide;

4-Hydroxy-3-$\beta$-D-(2′,3′,5′-tri-O-isobutyryl-ribofuranosyl)-$N_1$-isobutyrylpyrazole-5-carboxamide; and the like.

Mixed tetra-acylates, wherein $R_1$, $R_3$, and $R_4$ in the above general formula are different acyl groups, are prepared by mono-$N_1$-acylation of a protected pyrazofurin derivative, such as a 2′,3′-acetonide of pyrazofurin for example. The protected mono-$N_1$-acylate is then acylated at the 5′-position to provide the corresponding protected di-acylate, which is subsequently converted to the pyrazofurin mono-5′-O-acylate. The 5′-mono-O-acylate is then $N_1$-acylated and then further acylated at the 2' and 3' positions to provide the desired tetra-acylate. More specifically, pyrazofurin is converted to a 2',3'-protected derivative with any of a number of suitable protecting groups. A preferred protecting group, for example, is the isopropylidine group. Generally, pyrzaofurin can simply be treated with acetone in the presence of an acid, such as p-toluenesulfonic acid for instance, to provide the desired pyrazofurin 2',3'-acetonide. The protected pyrazofurin is then acylated at the $N_1$-position of the pyrazole ring, for example with an acylating agent such as an acid anhydride, under non-basic conditions and in a protic solvent such as methanol. The pyrazofurin mono-$N_1$-acylate 2',3'-acetonide so formed is subsequently further acylated at the 5'-position, for example with an acylating agent such as an acid anhydride or acid halide, in the presence of a weak base such as pyridine, for instance, thus providing a protected diacylated pyrazofurin derivative. Both the $N_1$-acyl group and the 2',3'-isopropylidine protecting groups are readily removed by solvolysis in a protic solvent, such as methanol or water for example. Generally, the 2',3'-isopropylidine group and the $N_1$-acyl group are solvolyzed when the pyrazofurin di-acylated acetonide is stirred in a protic solvent at about 30° to about 80°C. for a period of time of about 2 to about 20 hours. Removal of the solvent provides the product, a 4-hydroxy-3-$\beta$-D-(5'-O-acylribofuranosyl)pyrazole-5-carboxamide.

Examples of mono-5'-O-acylates of pyrazofurin include:

4-Hydroxy-3-$\beta$-D-(5'-O-acetylribofuranosyl)-pyrazole-5-carboxamide;

4-Hydroxy-3-$\beta$-D-(5'-O-benzoylribofuranosyl)-pyrazole-5-carboxamide;

4-Hydroxy-3-$\beta$-D-(5'-O-adamantoylribofuranosyl)-pyrazole-5-carboxamide;

4-Hydroxy-3-$\beta$-D-(5'-O-palmitoylribofuranosyl)-pyrazole-5-carboxamide;

4-Hydroxy-3-$\beta$-D-(5'-O-butyrylribofuranosyl)-pyrazole-5-carboxamide;

4-Hydroxy-3-$\beta$-D-(5'-O-hexanoylribofuranosyl)-pyrazole-5-carboxamide; and the like.

Acylation of the pyrazofurin mono-5'-O-acylate under non-basic conditions and in a protic solvent, such as methanol for example, provides a pyrazofurin di-acylated derivative, namely a 4-hydroxy-3-$\beta$-D-(5'-O-acylribofuranosyl)-$N_1$-acylpyrazole-5-carboxamide. Further acylation of the di-acylate, for example with an acid anhydride in the presence of a weak base such as pyridine, provides the corresponding tetra-acylated pyrazofurin derivative, namely a 2',3',5'-tri-O-acylate-$N_1$-acylate. By selecting different acylating agents at each step, a mixed tetra-acylate can be prepared if desired. Examples of mixed tetra-acylates include:

4-Hydroxy-3-$\beta$-D-(2',3'-di-O-acetyl-5'-O-n-butyrylribofuranosyl)-$N_1$-propinoylpyrazole-5-carboxamide;

4-Hydroxy-3-$\beta$-D-(2',3'-di-O-acetyl-5'-O-palmitoyl-ribofuranosyl)-$N_1$-N-butyrylpyrazole-5-carboxamide;

4-Hydroxy-3-$\beta$-D-(2',3'-di-O-n-butyryl-5'-O-acetyl-ribofuranosyl)-$N_1$-pivaloylpyrazole-5-carboxamide; and the like.

In another aspect of the invention, the mono-$N_1$-acylated derivative of pyrazofurin is further acylated to provide aa penta-acylate, specifically a 4,2',3',5'-tetra-O-acylate-$N_1$-acylate of pyrazofurin. The reaction generally is carried out under conditions similar to those used in the preparation of the tetra-acylate. In particular, a weak base such as pyridine is used when reacting the mono-$N_1$-acylate with the corresponding acylating agent, a preferred anhydride for instance, either in a solvent or by using the base and the acylating agent as the solvent. The reaction normally is conducted over a longer period of time, about 5 to about 20 hours, and the temperature generally is maintained at about 20° to about 30°C. Longer reaction times can be incorporated if desired. The acylating agent is incorporated in excess of the mono-$n_1$-acylate pyrazofurin derivative, generally in about a 10 to 20 molar excess; however, even more can be used if desired. Similarly, the base is used in excess, preferably in amounts sufficient to serve as a co-solvent with the acylating agent. The product penta-acylate is isolated by complete removal of any excess acylating agent, base, solvent, or the like, and usually the product needs no further purification. If desired, however, the pyrazofurin penta-acylate can be washed with aqueous solutions of acid or base, such as dilute mineral acid or dilute bicarbonate bases, for example. The product can be further purified if desired by chromatography and the like.

As hereinbefore indicated, the preferred penta-acylates are those wherein all acyl substituents are the same. Typical examples of such preferred penta-acylates include:

4-Acetoxy-3-$\beta$-D-(2',3',5'-tri-O-acetyl-ribofuranosyl)-$N_1$-acetylpyrazole-5-carboxamide, 4-n-Butyryloxy-3-$\beta$-D-(2',3',5'-tri-O-n-butyryl-ribofuranosyl)-$N_1$-n-butyrylpyrazole-5-carboxamide;

4-Isohexanoyloxy-3-$\beta$-D-(2',3',5'-tri-O-isohexanoyl-ribofuranosyl)-$N_1$-isohexanoylpyrazole-5-carboxamide; and the like.

Mixed penta-acylates can be prepared by selecting the appropriate starting materials. For example, acylation of a mono-$N_1$-acylate could provide a penta-acylate of the above formula wherein $R_2$, $R_3$, and $R_4$ are all the same acyl group, which is different from $R_1$. Further acylation of a mixed tetra-acylate, wherein $R_1$ is different from $R_3$ and $R_4$, provides a mixed penta-acylate wherein $R_1$ is different from $R_3$ and $R_4$, which are different from $R_2$. Examples of mixed penta-acylates include:

4-Acetoxy-3-$\beta$-D-(2',3',5'-tri-O-n-butyryl-ribofuranosyl)-$N_1$-acetylpyrazole-5-carboxamide;

4-Isopentanoyloxy-3-$\beta$-D-(2',3'-di-O-acetyl-5'-adamantoylribofuranosyl)-$N_1$-n-butyrylpyrazole-5-carboxamide; and 4-n-Hexanoyl-3-$\beta$-D-(2',3',5'-tri-O-acetyl-ribofuranosyl)-$N_1$-n-butyrylpyrazole-5-carboxamide.

As indicated hereinabove, the $N_1$-acyl group and the 4-acyl group of a pyrazofurin polyacylate generally are somewhat labile to protic solvents and are susceptible to cleavage by solvolysis. Conseqently, either the tetra-acylates or the penta-acylates, which are prepared as described hereinbefore, can be converted to tri-O-acylates by simple solvolysis in a suitable protic solvent. Typical solvents useful for such solvolysis reactions include water, alcohols, such as methanol or ethanol for instance, or mixtures of such protic solvents. The reaction generally is carried out by stirring the appropriate pyrazofurin tetra-acylate or penta-acylate in a protic solvent, preferably methanol or a methanol and water mixture, at an elevated temperature for several days. More particularly, the temperature of the reaction mixture is normally maintained below about 120°C., preferably in the range of about 30° to about 100° C. The reaction is conveniently carried out at the reflux temperature of the appropriate solvent. The solvolysis is normally substantially complete after about 1 to 10 days, depending to some extent upon the particular acyl group being cleaved. The reaction generally is allowed to continue for about 4 or 5 days. The product, a pyrazofurin 2′,3′,5′-tri-O-acylate, is recovered by complete removal of any reaction solvent. Further purification is generally not needed; however, further purification by procedures such as solid-liquid chromatography, thick-layer chromatography, crystallization, or the like, can be carried out if desired. While mixed tri-O-acylates can be prepared from the corresponding mixed tetra- or penta-acylate, the preferred tri-O-acylates are those wherein all three acyl groups are the same $C_1$–$C_6$ alkanoyl group. Examples of preferred tri-O-acylates of pyrazofurin include:

4-Hydroxy-3-$\beta$-D-(2′,3′,5′-tri-O-acetyl-ribofuranosyl)-pyrazole-5-carboxamide;

4-Hydroxy-3-$\beta$-D-(2′,3′,5′-tri-O-n-butyryl-ribofuranosyl)pyrazole-5-carboxamide;

4-Hydroxy-3-$\beta$-D-(2′,3′,5′-tri-O-isohexanoyl-ribofuranosyl)pyrazole-5-carboxamide.

Further in accordance with the present invention, a pyrazofurin mono-$N_1$-acylate can be acylated under the more vigorous acylation conditions of a strong base to provide tetra-acylates and penta-acylates wherein the 5-carboxamide group is acylated. A "strong base" as used herein refers to a base having a $pK'_b$ in the range of about 3 to about 4. Typical strong bases for the present process include certain amines such as triethylamine, isopropylamine, methyldiethylamine, ethylamine, dimethylamine, isoamylamine, and the like. Triethylamine is an especially preferred strong base in the present porcess. The amount of base used in the reaction is not critical; however, the base is usually used in excess of the mono-$N_1$ -acylate starting material, and generally in amounts sufficient to serve as solvent or co-solvent, in conjunction with the acylating agent. An additional solvent or co-solvent can be incorporated if desired. Suitable solvents include organic solvents such as aromatics, ethers, esters, amides, halogenated hydrocarbons, and the like. Typical solvents include, for example, benzene, toluene, dimethylacetamide, diethyl ether, ethyl acetate, chloroform, and the like.

Generally, the pyrazofurin mono-$N_1$-acylate and the acylating agent are commingled in a suitable strong base, such as triethylamine for example. The acylating agent is normally employed in amounts in excess of the mono-$N_1$-acylate, usually in about 10 to 20 molar excess. More acylating agent, or less, can be used if desired; however, at least a 4 molar excess is generally needed. The acylating agent, especially an acid anhydride, and the base are generally used in excessive amounts such as to serve as reaction solvent. When the acylating agent selected is an acid halide, the excess amounts of acylating agent is usually kept to a minimum, for example about a 4 molar excess. By varying the length of reaction, either a pyrazofurin tetra-acylate or a pyrazofurin penta-acylate is obtained, either of which is acylated at the pyrazole-5-carboxamide group. More specifically, when the acylation reaction is carried out at a temperature of about 0° to about 15°C., the pyrazofurin 2′,3′,5′-tri-O-acylate wherein the 5-carboxamide group is also acylated is obtained after a period of time of about ½ to about 2 hours. The temperature can be increased if desired, for example to about 25°C., but the reaction is best carried out at the lower temperature of about 0° to 15°C. The product is isolated by complete removal of any excess acylating agent, base, or other solvents. Generally, the product so obtained can be stirred in a protic solvent, such as aqueous methanol for example, thereby insuring complete conversion of any penta-acylate to the corresponding tetra-acylate. Further purification by standard procedures such as solid-liquid chromatography or thick layer chromatography can be carried out if desired. The preferred tetra-acylates are those wherein all four acyl groups are the same and are selected from among $C_1$–$C_6$ alkanoyl. Typical examples of preferred tetra-acylates of pyrazofurin include:

4-Hydroxy-3-$\beta$-D-(2′,3′,5′-tri-O-acetyl-ribofuranosyl)-pyrazole-5-N-acetylcarboxamide;

4-Hydroxy-3-$\beta$-D-(2′,3′,5′-tri-O-n-butyryl-ribofuranosyl)pyrazole-5-N-n-butyrylcarboxamide;

4-Hydroxy-3-$\beta$-D-(2′,3′,5′-tri-O-isohexanoyl-ribofuranosyl)pyrazole-5-N-isohexanoylcarboxamide; and the like.

Mixed tetra-acylates can be preapred if desired by selecting the proper acylating agent and further acylating a pyrazofurin 2′,3′,5′-tri-O-acylate-$N_1$-acylate in the presence of a strong base such as triethylamine.

In yet another aspect of the invention, a mono-$N_1$-acylate of pyrazofurin can be acylated uner conditions of strong base at temperatures of about 20° to 30°C. for longer periods of time, to provide a penta-acylate, namely, a pyrazofurin 2′,3′,5′-tri-O-acylate-$N_1$-acylate wherein the carboxamide group is also acylated. More specifically, a pyrazofurin mono-$N_1$-acylate is treated with an acylating agent, for example, an acid anhydride, in the presence of a strong base such as triethylamine, for a period of time from about 20 to about 100 hours, to provide the corresponding penta-acylate. The acylating agent is generally used in about 10 to 20 molar excess of the starting mono-$N_1$-acylate, and the base is normally employed in quantities sufficient to serve as solvent, as described hereinbefore. The reaction is normally complete after about 36 hours when conducted at a temperature of about 25°C. Isolation of the penta-acylate is accomplished by complete removal of the solvent, and further purification is generally not needed, but can be accomplished by standard procedures such as chromatography if desired. As indicated hereinabove, the preferred polyacylates of the invention are those wherein all of the acyl groups present are the same. Typically preferred penta-acylates of the above formula wherein $R_1$, $R_3$, $R_4$ and $R_5$ are acyl groups include:

4-Hydroxy-3-$\beta$-D-(2′,3′,5′-tri-O-acetyl-ribofuranosyl)-$N_1$-acetylpyrazole-5-N-acetylcarboxamide;

4-Hydroxy-3-$\beta$-D-(2′,3′,5′-tri-O-n-butyryl-ribofuranosyl)-$N_1$-n-butyrylpyrazole-5-N-n-butyrylcarboxamide;

4-Hydroxy-3-$\beta$-D-(2′,3′,5′-tri-O-isohexanoyl-ribofuranosyl)-$N_1$-isohexanoylpyrazole-5-N-isohexanoylcaboxamide; and the like.

Mixed penta-acylates can be prepared, if desired, by further acylating a mixed tetra-acylate in the presence of a strong base such as triethylamine. As with other mixed acylates, however, these mixed penta-acylates are sometimes more difficult to purify and, conseqently, are the least preferred penta-acylates.

The novel compounds of this invention are active against various viruses, fungi and are especially useful for the treatment of psoriasis. The compounds can be formulated so as to facilitate convenient administration. The compounds are especially suited to topical application when treating psoriasis, due to the substantially complete topical absorption of the compounds of the invention. The active ingredient can be employed in combination with one or more adjuvants, diluents, or carriers. For topical application, the active component is generally commingled with diluents and formulated as an ointment or a cream. Typical diluents used in ointment preparations include oleaginous ointment bases such as white petrolatum, polyethylene glycols, lanolin, and the like. Generally, the compound of the invention will be formulated in quantities of about 0.01 to about 2 percent by weight. The compound of the invention is most conveniently formulated into tablets or capsules for oral administration. Such tablets or capsules will consist of a compound of this invention as the active ingredient, generally mixed with a carrier or diluent. Examples of diluents or carriers which may be employed in the pharmaceutical compositions of the present invention are lactose, dextrose, sucrose, sorbital, mannitol, propylene glycol, liquid paraffin, calcium phosphate, microcrystalline cellulose, gelatin, ethyl lactate, and the like. A typical tablet or capsule, for example, will contain from about 300 to 1000 mg. of active ingredient mixed with a suitable carrier or diluent. In the treatment of psoriasis, the dosages wiell be administered about once or twice per week. The compounds of the invention can be formulated for parenteral administration, preferably intravenous, with a suitable carrier or diluent. Generally, the active ingredient will be administered in amounts of about 300 to 1000 mg. per patient one or two times each week for psoriasis. It should be noted that the amount of compound of this invention actually to be administered will be determined in light of the relevant circumstances surrounding a particular case, such as the condition to be treated, the particular compound selected, the route of administration, and the like.

The preparation of these compounds is more fully described in the following detailed examples. It is to be understood, however, that the examples are illustrative of the compounds embraced by this invention and of the methods for their preparation and are not to be construed as limiting the invention to the particular compounds or methods specifically described.

EXAMPLE 1

4-Hydroxy-3-β-D-ribofuranosyl-N₁-acetylpyrazole-5-carboxamide

A solution of 1.0 g. of 4-hydroxy-3-β-D-ribofuranosylpyrazole-5-carboxamide in 20 cc. of anhydrous methyl alcohol was stirred and cooled to 0°C. To the cold stirred solution was added 5 cc. of acetic anhydride dropwise over about 10 minutes. The reaction mixture was stirred for about 1 hour while the temperature was allowed to increase to about 25°C. The solvent was removed under reduced pressure to provide an oily residue which was dissolved in 25 cc. of 50 percent methanol-toluene. Again the solvent was removed under reduced pressure. This procedure was repeated three times to insure complete removal of any excess acylating agent. After the final solvents were totally removed, 4-hydroxy-3β-D-ribofuranosyl-N₁-acetylpyrazole-5-carboxamide remained as a white solid.

M/e theory 301; found: 301. nmr (CDCl₃): (140 Hz,

EXAMPLE 2

4-Hydroxy-3-β-D-ribofuranosyl-N₁-n-butryryl-pyrazole-5-carboxamide was prepared by the procedure of Example 1 from butyric anhydride.
nmr (D₂O): (60 Hz, t, 3H, —CH₃)
(100 Hz, m, 2H, —CH₂—)
(161 Hz, t, 2H,

EXAMPLE 3

4-Hydroxy-3-β-D-(2',3',5'-tri-O-acetylribofuranosyl)-N₁-acetylpyrazole-5-carboxamide A solution of 1.0 g. of 4-hydroxy-3-β-D-ribofuranosyl-N₁-acetylpyrazole-5-carboxamide in 10 cc. of dry pyridine was cooled to 0°C. and stirred while 8 cc. of acetic anhydride was added dropwise over about 10 minutes. The reaction mixture was stirred for 2 hours at 0°C., after which time the solvent was removed under reduced pressure to provide an oily residue. The residue was dissolved in 50 cc. of a 50 percent solution of methanol-benzene, and the solvent was removed under reduced pressure. This procedure was repeated three times to insure complete removal of excess acylating agent. After complete solvent removal, the residue was dissolved in 25 cc. of water and extracted therefrom with three 25 cc. portions of chloroform. The chloroform extracts were combined, washed with 25 cc. of 0.1 N hydrochloric acid, 25 cc. of aqueous saturated sodium bicarbonate solution, and dried. The solvent was removed under reduced pressure to provide 4-hydroxy-3-β-D-(2',3',5'-tri-O-acetylribofuranosyl)-N₁-acetylpyrazole-5-carboxamide as a white amorphous solid.

M/e theory: 427; found: 427.
nmr (CDCl₃): (140 Hz, s, 3H,

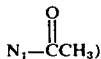

(125 Hz, m, 9H,

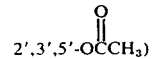

EXAMPLE 4

4-Acetoxy-3-β-D-(2',3',5'-tri-O-acetylribofuranosyl)-N₁-acetylpyrazole-5-carboxamide To a cooled solution of 1.0 g. of 4-hydroxy-3-β-D-ribofuranosyl-N₁-acetylpyrazole-5-carboxamide in 10 cc. of dry pyridine was added 8 cc. of acetic anhydride dropwise over about 10–15 minutes. The reaction mixture was allowed to warm to about 25°C. and stirring was continued for about 12 hours. The solvent was removed under reduced pressure to provide an oily residue which was dissolved in 20 cc. of an ice-water mixture. The aqeuous solution was extracted three times with 25 cc. portions of chloroform. The chloroform extracts were combined and washed with 25 cc. of 0.1 N hydrochloric acid solution and then twice with 20 cc. portions of aqueous saturated sodium bicarbonate solutions. After drying the organic solution, the solvent was removed under reduced pressure to afford 4-acetoxy-3β-D-(2',3',5'-tri-O-acetylribofuranosyl)-N₁-acetylpyrazole-5-carboxamide as a white solid.

M/e theory: 469; found: 469.

nmr (CDCl₃):

(140 Hz, s, 3H,

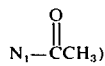

(164 Hz, s, 3H,

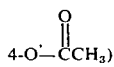

(125 Hz, m, 9H,

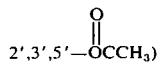

EXAMPLE 5

4-n-Butyroxy-3-β-D-(2',3',5'-tri-O-n-butyryl-ribofuranosyl)-N₁-n-butyrylpyrazole-5-carboxamide A solution of 0.5 g. of 4-hydroxy-3-β-D-ribofuranosyl-N₁-n-butyrylpyrazole-5-carboxamide in 5 cc. of dry pyridine was stirred and cooled to 0°C. while 4cc. of butyric anhydride was added dropwise to the reaction mixture during 5 minutes. The temperature of the reaction mixture was allowed to rise to about 25°C. after the addition of the butyric anhydride was complete, and the reaction mixture was stirred at 25°C. for six hours. The reaction mixture was concentrated to dryness under reduced pressure to provide a residue which was dissolved in 20 cc. of an ice-water mixture and 25 cc. of chloroform. The organic layer was separated and the aqueous layer was further extracted with two 25 cc. portions of chloroform. The organic extracts were combined and washed with 0.1 N hydrochloric acid solution, saturated aqueous sodium bicarbonate solution, dried, and evaporated to dryness under reduced pressure, providing 4-n-butyroxy-3-β-D-(2',3',5'-tri-O-n-butyrylribofuranosyl)-N₁-n-butyrylpyrazole-5-carboxamide as a colorless oil.

M/e therory: 609; found: 609.

EXAMPLE 6

4-Acetoxy-3-β-D-(2',3',5'-tri-O-acetylribofuranosyl)-N₁-n-butyrylpyrazole-5-carboxamide A solution of 329 mg. of 4-hydroxy-3-β-D-ribofuranosyl-N₁-n-butyrylpyrazole-5-carboxamide in 10 cc. of dry pyridine was stirred and cooled to 0°C. while 5 cc. of acetic anhydride was added dropwise to the stirred solution during 5 minutes. The reaction mixture was warmed to 25°C. during 1 hour, and stirred at 25°C. for 4 hours. The solvent was removed under reduced pressure, leaving a residue which was dissolved in 30 cc. of water. The product was extracted into chloroform. The chloroform extracts were combined and washed with saturated aqueous sodium bicarbonate and dried. Removal of the solvent afforded 4-acetoxy-3-β-D-(2',3',5'-tri-O-acetylribofuranosyl)-N₁-n-butyrylpyrazole-5-carboxamide.

EXAMPLE 7

4-Hydroxy-3-β-D-(2',3',5'-tri-O-acetylribofuranosyl)-pyrazole-5-carboxamide

A solution of 5.0 g. of 4-acetoxy-3-β-D-(2',3',5'-tri-O-acetylribofuranosyl)-N₁-acetylpyrazole-5-carboxamide in 100 cc. of methyl alcohol was heated at reflux for 6 days. The solution was cooled to about 25°C. and the solvent was removed under reduced pressure to provide 4-hydroxy-3-β-D-(2',3', 5'-tri-O-acetylribofuranosyl)pyrazole-5-carboxamide.

M/e theory: 385; found: 385.

nmr (CDCl₃): (125 Hz, m, 9H,

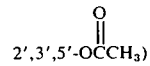

EXAMPLE 8

Following the procedure set forth in Example 7, 4-hydroxy-3-β-D-(2',3',5'-tri-O-n-butyrylribofuranosyl)-N₁-n-butyrylpyrazole-5-carboxamide was converted to 4-hydroxy-3-β-D-(2',3',5'-tri-O-n-butyryl-ribofuranosyl)pyrazole-5-carboxamide.

EXAMPLE 9

4-Hydroxy-3-β-D-ribofuranosylpyrazole-5-carboxamide 2',3'-acetonide

To a stirred suspension of 518 mg. of 4-hydroxy-3-β-D-ribofuranosylpyrazole-5-carboxamide and 15 cc. of acetone was added in one portion 38 mg. of p-toluenesulfonic acid. The reaction mixture was stirred for 16 hours at 25°C. Two cc. of 2,2-diethoxypropane was added to the reaction mixture in order to help drive the reaction to completion. The reaction mixture was stirred an additional 24 hours at 25°C. To the stirred reaction mixture was added 1 cc. of concentrated ammonium hydroxide solution, and stirring was continued for about 15 minutes, after which time the solvent was removed under reduced pressure, affording a crude product. Further purification was accomplished by preparative thick layer chromatography on silica gel coated glass plates, eluting with chloroform. The major component was the 2',3'-acetonide of 4-hydroxy-3-β-D-ribofuranosylpyrazole-5-carboxamide.

nmr (CDCl₃): (87 Hz and 100 Hz, 6H C(CH₃)₂)

EXAMPLE 10

4-Hydroxy-3-β-D-(5'-n-butryrylribofuranosyl)-pyrazole-5-carboxamide

A solution of 4-hydroxy-3-β-D-ribofuranosyl-N₁-acetylpyrazole-5-carboxamide 2',3'-acetonide in 5 cc. of dry pyridine was stirred and cooled to 0°C. while 1 cc. of butyric anhydride was added to the reaction mixture during 2 minutes. The reaction mixture was stirred for 6 hours at 0°C. The solvents were removed under reduced pressure, affording 4-hydroxy-3-β-D-(5'-O-n-butyrylribofuranosyl)-N₁-acetylpyrazole-5-carboxamide 2',3'-acetonide as a residue, which was then dissolved in 20 cc. of 50 percent aqueous methanol and heated at reflux for 10 hours. The solvents were removed under reduced pressure and the product was dissolved in 25 cc. of 50 percent methanol-toluene. The solvents were again removed under reduced pressure, providing 4-hydroxy-3-β-D-(5'-o-n-butyrylribofuranosyl)pyrazole-5-carboxamide.

EXAMPLE 11

4-Hydroxy-3-β-D-(5'-O-palmitoylribofuranosyl)-pyrazole-5-carboxamide

A solution of 319 mg. of 4-hydroxy-3-β-D-ribofuranosyl-N$_1$-acetylpyrazole-5-carboxamide 2',3'-acetonide was dissolved in 5 cc. of dimethylacetamide containing 325 mg. of palmitoyl chloride. The reaction mixture was stirred at room temperature for 72 hours. The solvent was removed under reduced pressure, providing an oily residue which was dissolved in 20 cc. of 50 percent aqueous methanol and stirred for 16 hours at room temperature. The solvent was removed under reduced pressure, and the product was extracted into chloroform and washed with saturated aqueous sodium bicarbonate solution and with water, and dried. Removal of the solvent under reduced pressure provdied 4-hydroxy-3-β-D-(5'-O-palmitoylribofuranosyl)-pyrazole-5-carboxamide.

EXAMPLE 12

4-Hydroxy-3-β-D-(2',3',5'-tri-O-acetylribofuranosyl)-N$_1$-acetylpyrazole-5-N-acetylcarboxamide.

A solution of 1.0 g. of 4-hydroxy-3-β-D-ribofuranosyl-N$_1$-acetylpyrazole-5-carboxamide in 10 cc. of acetic anhydride was stirred and cooled to 0°C. and 3 cc. of triethylamine was added in one portion to the reaction mixture. The reaction mixture was allowed to warm to 25°C. and stirring was continued for 48 hours. Removal of the solvent under reduced pressure provided an oily residue which was redissolved in 25 cc. of a 50 percent solution of benzene-dichloromethane. The solvent was again removed under reduced pressure. The residue was dissolved in 50 cc. of chloroform and washed with water, 0.1 N hydrochloric acid solution, saturated aqueous sodium bicarbonate solution, and dried. Removal of the solvent under reduced pressure provided a thick syrup which was then dissolved in 2 cc. of chloroform and applied to a column packed with 30 g. of silica gel (Woelm Grade 1). The column was first eluted with 1 liter of hexane, followed by elution with 1 liter of 50 percent hexane-benzene, then with 1 liter of 90 percent benzene-ethyl acetate, 1 liter of 75 percent benzene-ethyl acetate, 1 liter of 50 percent benzene-ethyl acetate, and finally with 1 liter of ethyl acetate. The fractions eluted with 50 percent benzene-ethyl acetate were combined and the solvent was removed under reduced pressure, providing 800 mg. of 4-hydroxy-3-β-D-(2',3',5'-tri-O-acetylribofuranosyl)-N$_1$-acetylpyrazole-5-N-acetylcarboxamide.

nmr (CDCl$_3$): (157 Hz, s, 3H,

(140 Hz, s, 3H,

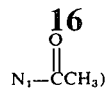

(125 Hz, s, 9H,

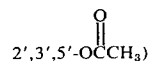

The ethyl acetate eluate fractions were combined and the solvent was removed therefrom under reduced pressure, affording 395 mg. of 4-hydroxy-3-β-D-(2',-3',5'-tri-O-acetylribofuranosyl)pyrazole-5-N-acetylcarboxamide.

nmr (CDCl$_3$): (157 Hz, s, 3H,

(125 Hz, s, 9H,

EXAMPLE 13

4-Hydroxy-3-β-D-(2',3',5'-tri-O-acetylribofuranosyl)-pyrazole-5-N-acetylcarboxamide Triethylamine was added to a solution of 4-hydroxy-3-β-D-ribofuranosyl-N$_1$-acetylpyrazole-5-carboxamide in acetic anhydride at 0°C. The reaction mixture was warmed to about 10°C. and stirred for 1 hour. The reaction mixture was concentrated under reduced pressure to provide an oily residue which was redissolved in a benzene-dichloromethane solution and again the solvent was removed. The resulting residue was dissolved in a 20 percent methanol in water solution and stirred for 5 hours. The solvents were completely removed under reduced pressure to provide 4-hydroxy-3-β-D-(2',3',5'-tri-O-acetylribofuranosyl)pyrazole-5-N-acetylcarboxamide.

I claim:
1. The compound having the formula

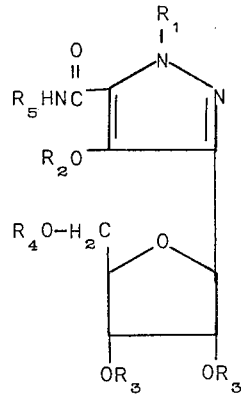

wherein:
R$_1$, R$_2$, R$_3$, and R$_5$ independently are hydrogen or C$_1$–C$_6$ alkanoyl;

$R_4$ is hydrogen, $C_1$–$C_6$ alkanoyl, palmitoyl, benzoyl, or adamantoyl;

with the limitations that at least one of $R_1$, $R_2$, $R_3$, $R_4$, or $R_5$ is a group other than hydrogen, that $R_2$ is alkanoyl only when $R_1$ is alkanoyl, that $R_3$ is alkanoyl only when $R_4$ is alkanoyl, and that $R_5$ is alkanoyl only when $R_3$ and $R_4$ are both alkanoyl.

2. The compound of the formula

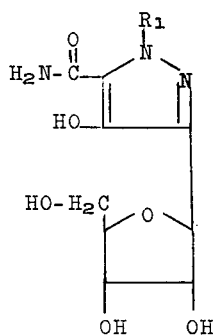

wherein $R_1$ is $C_1$–$C_6$ alkanoyl.

3. The compound of claim 2, wherein $R_1$ is acetyl.
4. The compound of claim 2, wherein $R_1$ is n-butyryl.
5. The compound of claim 1, wherein $R_1$, $R_3$, and $R_4$ are $C_1$–$C_6$ alkanoyl and $R_2$ and $R_5$ are hydrogen.
6. The compound of claim 5, wherein $R_1$, $R_3$, and $R_4$ are the same.
7. The compound of claim 6, wherein $R_1$, $R_3$, and $R_4$ are acetyl.
8. The compound of claim 6, wherein $R_1$, $R_3$, and $R_4$ are n-butyryl.
9. The compound o claim 1, wherein $R_3$ and $R_4$ are $C_1$–$C_6$ alkanoyl, and $R_1$, $R_2$ and $R_5$ are hydrogen.
10. The compound of claim 9, wherein $R_3$ and $R_4$ are the same.
11. The compound of claim 1, wherein $R_1$, $R_2$, $R_3$, and $R_4$ are $C_1$–$C_6$ alkanoyl, and $R_5$ is hydrogen.
12. The compound of claim 11, wherein $R_1$, $R_2$, $R_3$, and $R_4$ are the same $C_1$–$C_6$ alkanoyl group.
13. The compound of claim 1, wherein $R_3$, $R_4$, and $R_5$ are $C_1$–$C_6$ alkanoyl and $R_1$ and $R_2$ are hydrogen.
14. The compound of claim 13, wherein $R_3$, $R_4$ and $R_5$ are the same.
15. The compound of claim 14, wherein $R_3$, $R_4$, and $R_5$ are acetyl groups.
16. The compound of claim 14, wherein $R_3$, $R_4$, and $R_5$ are n-butyryl groups.
17. The compound of claim 1, wherein $R_1$, $R_3$, $R_4$, and $R_5$ are $C_1$–$C_6$ alkanoyl, and $R_2$ is hydrogen.
18. The compound of claim 17, wherein $R_1$, $R_3$, $R_4$, and $R_5$ are the same alkanoyl group.
19. The compound of claim 18, wherein $R_1$, $R_3$, $R_4$, and $R_5$ are acetyl.
20. The compound of claim 18, wherein $R_1$, $R_3$, $R_4$, and $R_5$ are n-butyryl.
21. The compound of claim 1, wherein $R_1$, $R_2$, $R_3$ and $R_5$ are hydrogen.

* * * * *